US006958119B2

(12) United States Patent
Yin et al.

(10) Patent No.: US 6,958,119 B2
(45) Date of Patent: Oct. 25, 2005

(54) MOBILE PHASE GRADIENT GENERATION MICROFLUIDIC DEVICE

(75) Inventors: Hongfeng Yin, San Jose, CA (US); Kevin Killeen, Palo Alto, CA (US); Daniel Sobek, Portola Valley, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 101 days.

(21) Appl. No.: 10/085,598

(22) Filed: Feb. 26, 2002

(65) Prior Publication Data

US 2003/0159993 A1 Aug. 28, 2003

(51) Int. Cl.[7] ............................................. B01D 15/08
(52) U.S. Cl. .................... 210/198.2; 210/101; 210/656
(58) Field of Search ...................... 210/198.2, 656, 210/101, 143; 422/70, 100; 95/82; 96/101; 251/304; 137/625.46

(56) References Cited

U.S. PATENT DOCUMENTS

| | | | | |
|---|---|---|---|---|
| 4,891,120 A | * | 1/1990 | Sethi et al. .................. 204/600 |
| 4,908,112 A | * | 3/1990 | Pace ........................ 210/198.2 |
| 4,942,018 A | | 7/1990 | Munk .......................... 422/70 |
| 5,132,012 A | * | 7/1992 | Miura et al. .............. 210/198.2 |
| 5,253,981 A | * | 10/1993 | Yang et al. ..................... 417/3 |
| 5,291,226 A | | 3/1994 | Schantz et al. ......... 346/140 R |
| 5,305,015 A | | 4/1994 | Schantz et al. ............. 346/101 |
| 5,595,650 A | * | 1/1997 | Manz ...................... 210/198.2 |
| 5,630,706 A | * | 5/1997 | Yang ............................ 417/3 |
| 5,658,413 A | | 8/1997 | Kaltenbach et al. ..... 156/272.8 |
| 5,664,938 A | * | 9/1997 | Yang .......................... 417/313 |
| 5,705,813 A | | 1/1998 | Apffel et al. ............... 250/288 |
| 5,716,825 A | | 2/1998 | Hancock et al. ......... 435/286.5 |
| 5,872,010 A | * | 2/1999 | Karger et al. ............... 436/173 |
| 5,882,571 A | | 3/1999 | Kaltenbach et al. ........ 264/400 |
| 5,935,430 A | * | 8/1999 | Craig ...................... 210/198.2 |
| 6,012,902 A | * | 1/2000 | Parce .......................... 417/48 |
| 6,033,546 A | | 3/2000 | Ramsey ..................... 204/603 |
| 6,110,343 A | * | 8/2000 | Ramsey et al. ............. 204/601 |
| 6,245,227 B1 | * | 6/2001 | Moon et al. .............. 210/198.2 |
| 6,258,263 B1 | * | 7/2001 | Henderson et al. ....... 210/198.2 |
| 6,323,042 B1 | * | 11/2001 | Narang et al. .............. 436/514 |
| 6,440,284 B1 | * | 8/2002 | Dubrow ...................... 204/455 |
| 6,581,441 B1 | * | 6/2003 | Paul .......................... 73/61.52 |
| 6,627,076 B2 | * | 9/2003 | Griffiths ................... 210/198.2 |
| 6,702,256 B2 | * | 3/2004 | Killeen et al. .............. 251/304 |
| 6,845,968 B2 | * | 1/2005 | Killeen et al. .............. 251/304 |
| 2001/0042712 A1 | | 11/2001 | Battrell et al. .............. 210/511 |
| 2003/0017609 A1 | | 1/2003 | Yin et al. .................... 436/161 |

FOREIGN PATENT DOCUMENTS

| | | | | |
|---|---|---|---|---|
| WO | WO 93/17328 | | 2/1992 | .............. 210/198.2 |
| WO | WO 01/001025 | * | 1/2004 | .............. 210/198.2 |

OTHER PUBLICATIONS

M. T. Davis, et al., "Low Flow High–Performance Liquid Chromatography Solvent Delivery System Designed for Tandem Capillary Liquid"; Journal of the American Society for Mass Spectrometry, US, vol. 6, No. 7, Jul. 1, 1995; pp. 571–577.

Kutter et al. (1998), "Solvent–Programmed Microchip Open–Channel Electrochromatography," *Anal. Chem.* 70:3291–3297.

Whitesides et al. (2001), "Flexible Methods for Microfluidics," *Physics Today* 52(6):42–47.

* cited by examiner

*Primary Examiner*—Ernest G. Therkorn

(57) ABSTRACT

The present invention relates to a microfluidic device for separating the components of a fluid sample. A cover plate is arranged over the first surface of a substrate, which, in combination with a microchannel formed in the first surface, defines a separation conduit for separating the components of the fluid sample. An inlet port in fluid communication with the separation conduit allows a mobile phase containing a gradient of a selected mobile-phase component to be introduced from an integrated gradient-generation means to the separation conduit. A method is also provided for separating the components of a fluid sample using a mobile phase containing a gradient of a selected mobile-phase component, wherein the gradient is generated within a small volume of mobile phase.

28 Claims, 8 Drawing Sheets

MOBILE PHASE GRADIENT GENERATION MICROFLUIDIC DEVICE

TECHNICAL FIELD

The present invention generally relates to microfluidic devices that employ a mobile phase containing differing concentrations of a selected mobile-phase component. In particular, the invention relates to microfluidic devices that separate a fluid sample into its constituent components, wherein the employed mobile phase exhibits a concentration gradient of a selected mobile-phase component. In addition, the invention relates to the use of microfluidic devices to generate a gradient or differing concentrations of a selected mobile-phase component within a small volume of mobile phase in order to separate the components of a fluid sample.

BACKGROUND

Microfluidic device technologies, also referred to as lab-on-a-chip technologies, have been proposed for a number of different applications in various fields. In the field of biology, for example, microfluidic devices may be used to carry out cellular assays. In addition, microfluidic devices have been proposed to carry out separation techniques in the field of analytical chemistry.

Generally, microfluidic devices may be used to separate the components of a fluid sample using either of two techniques: capillary electrophoresis or chromatography. Capillary electrophoresis involves the separation of molecules based on differences in the electrophoretic mobility of the molecules. Typically, microfluidic devices employ a controlled application of an electric field to induce fluid flow and/or to provide flow switching. In order to effect reproducible and/or high-resolution separation, a fluid sample "plug" (a predetermined volume of fluid sample) must be controllably injected into a capillary separation column or conduit. For fluid samples containing high molecular weight charged biomolecular analytes, such as DNA fragments and proteins, microfluidic devices containing a capillary electrophoresis separation conduit that is a few centimeters in length may be effectively used to carry out separation of small sample plugs having a length on the order of micrometers. Once injected, high sensitivity detection, such as laser-induced fluorescence, may be employed to resolve a separated fluorescent-labeled sample component.

For samples containing analyte molecules with low electrophoretic mobility differences, such as those containing small drug molecules, the separation technology of choice is generally chromatography. Chromatographic separation occurs when a mobile phase carries sample molecules through a chromatography bed (stationary phase) where sample molecules interact with the stationary phase surface. The velocity at which a particular sample component travels through a chromatography bed depends on the component's partition between mobile phase and stationary phase. Microfluidic devices that incorporate a liquid chromatographic functionality have been described in U.S. Ser. No. 09/908,231. These microfluidic devices may employ integrated mechanical valve technologies, such as those described in U.S. Ser. No. 09/908,292, for sample introduction and to reduce the volume of "dead space" in the microfluidic devices.

There are many chromatographic techniques known in the art. See e.g., Kutter et al. (1998), "Solvent-programmed microchip open-channel electrochromatography," *Anal. Chem.* 70:3291–3297. For example, in reverse phase liquid chromatography, where the stationary phase offers a hydrophobic surface and the mobile phase is usually a mixture of water and an organic solvent, the least hydrophobic component moves through the chromatography bed first, followed by other components, in order of increasing hydrophobicity. In other words, the chromatographic separation of sample components may be based on hydrophobicity.

In isocratic liquid chromatography, the content of the mobile phase is constant throughout the separation. Gradient liquid chromatography, on the other hand, requires the content of the mobile phase to change during separation. Gradient liquid chromatography not only offers high resolution and high-speed separation of wide ranges of compounds, it also allows injection of large sample volumes without compromising separation efficiency. During the initial period when the sample is introduced, the mobile phase strength is often kept low, and the sample is trapped at the head of the liquid chromatography column bed. As a result, interfering moieties, such as salts, are washed away. In this regard, gradient liquid chromatography is suited to analyze fluid samples containing a low concentration of analyte moieties.

Typically, pressurizing means are employed to provide flow through packed columns in liquid chromatography. Such pressurizing means typically include pumps that are designed for optimal performance at a certain flow rate range, generally between about 50 $\mu$L/min to about 1 mL/min. To generate a gradient of a selected mobile-phase component within a mobile phase, two pumps may be employed to pump two fluids, each fluid containing a different concentration of the selected mobile-phase component. The fluids are mixed to form the mobile phase and introduced into the column. By varying the relative flow rate of the pumps, a concentration gradient of the selected mobile-phase component may be formed within the mobile phase flowing through the column. However, the quality of the gradient generated by this technique is limited by the performance of the pumps. In some cases, a gradient may require a fluid flow rate that lies outside the capability of the pumps. This limitation is particularly pronounced when microbore liquid chromatography columns are employed, because the required mobile-phase flow rate through the columns is extremely low.

Use of conventional chromatographic equipment with microfluidic devices for separating the components of a fluid may present other technical problems. For example, in order to obtain a smooth gradient, conventional liquid chromatography systems employ a pressure damper as well as a mixer. The pressure damper and the mixer require a certain volume of fluid for proper operation. This volume is associated with a delay time, i.e., the time it takes for a mobile phase to reach the liquid chromatography column after mixing. The delay time can be calculated as the quotient of the delay volume over the flow rate. For example, the combined volume of the damper and the mixer in a conventional liquid chromatography system is about 0.3 mL to about 0.5 mL. This translates to a delay time of about 0.3 minutes to about 0.5 minutes at a flow rate of 1 mL/min. However, if a microfluidic device is constructed for operation at a flow rate of less than about 1 $\mu$L/min, the delay time increases to about 300 minutes to about 500 minutes. Such a long delay time renders microfluidic device-based gradient liquid chromatography impractical.

To overcome this limitation, commercial low flow rate liquid chromatography pumps typically employ a split flow design. In this design, pumps move mobile phase at a high flow rate, but only a portion of the mobile phase is delivered to the separation column. The remainder of the mobile phase is diverted into a waste stream. This adds to the cost of operation because typically less than 1% of the mobile phase is actually used for separation.

In addition, the concentration of the selected mobile-phase components delivered to the column changes as gradient liquid chromatography is carried out. In most cases, the viscosity of the mobile phase also changes. This tends to change the pressure profile within the column. To compensate for such pressure profile changes, an electronic flow control unit that includes a flow meter and a variable flow resistor is used to control commercial chromatography pumps. As mobile phase is delivered to the column, the flow meter measures the flow rate of the mobile phase to provide feedback control over the variable flow resistor. Nevertheless, current flow sensor technologies are incapable of accurately measuring flow rates of less than 1 $\mu$L/min, especially in gradient mode, and are therefore unsuitable for use in microfluidic devices that are employed in gradient chromatography.

Thus, there is a need for integrated microfluidic device technology that allows control and generation of a gradient of a selected mobile-phase component within a small volume of mobile phase in order to separate the components of a fluid sample. In particular, there is a need for an improved microfluidic device that employs a smooth gradient at low flow rates, especially in flow rate ranges of less than 1 $\mu$L/min.

SUMMARY OF THE INVENTION

In a first embodiment, the invention relates to a microfluidic device for separating the components of a fluid sample. The microfluidic device comprises a substrate having a microchannel formed in a surface thereof and a cover plate arranged over the substrate surface. The cover plate, in combination with the microchannel, defines a separation conduit for separating the components of the fluid sample according to a specific component property. The microfluidic device also includes an integrated gradient-generation means for generating a gradient of a selected mobile-phase component in a mobile phase. The integrated gradient-generation means is arranged to allow the mobile phase from the gradient-generation means to be transported through an inlet port into the separation conduit and out of an outlet port. Typically, though not necessarily, the integrated gradient-generation means is formed at least in part within the substrate and/or in the cover plate.

In another embodiment, the invention relates to a microfluidic device that employs a gradient-generation means for generating a gradient of a selected mobile-phase component in a mobile phase in order to separate the components of the fluid sample. The gradient-generation means is formed from a substrate and a cover plate arranged over a surface of the substrate. A microchannel having an upstream terminus and a downstream terminus is formed in the surface of the substrate. The cover plate, in combination with the microchannel, forms a mobile-phase holding conduit having a length defined by the upstream terminus and the downstream terminus. A plurality of inlet ports is arranged along the length of the mobile-phase holding conduit, and an outlet port is located downstream from the inlet ports. A separation conduit is provided as well for separating the components of a fluid sample according to a specific component property, and a mobile-phase introducing means allows mobile phase from the mobile-phase holding conduit to flow through its outlet port and into a separation conduit.

In a further embodiment, the invention relates to a microfluidic device having an integrated mobile-phase source. The microfluidic device comprises a substrate having a microchannel formed in a surface thereof and a cover plate arranged over the substrate surface. The cover plate, in combination with the microchannel, defines a separation conduit for separating the components of the fluid sample according to a specific component property, and has an inlet port and an outlet port. An integrated mobile-phase source is provided comprising a microconduit having a length defined by an upstream terminus and a downstream terminus. The microconduit contains a mobile phase that exhibits a gradient of a selected mobile-phase component along the length of the microconduit. The integrated mobile-phase source is arranged to allow the mobile phase to be transported through the inlet port into the separation conduit and out of the outlet port.

In a still further embodiment, the invention relates to a method for separating the components of a fluid sample. The method uses no more than about 100 $\mu$L of fluid to produce a mobile phase containing a gradient of the selected mobile-phase component. Preferably, no more than about 20 $\mu$L of fluid is used to produce the gradient-containing mobile phase. The gradient-containing mobile phase produced as a result is used to convey a fluid sample through the separation conduit, thereby separating the components of the fluid sample.

In another embodiment, the invention relates to a microfluidic device for producing a flow of mobile phase. The device comprises a mobile-phase source and a pressurizing means. The mobile-phase source comprises a mobile-phase holding microconduit having a length defined by an upstream terminus and a downstream terminus, and an outlet port located at the downstream terminus, and a mobile phase, contained in the mobile-phase holding microconduit, that exhibits differing concentrations of selected mobile-phase component along the length of the mobile-phase holding microconduit. The pressurizing means allows for the pressurization of the microconduit to force the mobile phase within the microconduit to flow toward the downstream terminus along the length of the microconduit and out the outlet port.

In still another embodiment, the invention relates to a microfluidic device for producing a flow of mobile phase. The microfluidic device comprises, a producing means for producing different concentrations of a selected mobile-phase component in different locations within a mobile phase comprising, a plurality of mobile-phase sources, a mobile-phase introducing means and a pressurizing means. The producing means comprises a mobile-phase-holding microconduit having a length defined by an upstream terminus and a downstream terminus, an outlet port located at the downstream terminus, and at least one inlet port in fluid communication with the mobile-phase holding microconduit upstream from the outlet port. Each mobile-phase source contains a mobile phase of a different concentration of a selected mobile-phase component. The introduction means introduces plugs of mobile phase from the mobile-phase sources through the at least one inlet port into the mobile-phase holding conduit such that the plugs are arranged in a predetermined order along the length of the mobile-phase holding conduit. The pressurizing means pressurizes the microconduit to force the mobile phase within the microconduit to flow toward the downstream terminus along the length of the microconduit and out the single outlet port.

Thus, the invention provides, in yet another embodiment, a method for producing a flow of mobile phase. A mobile-phase source is provided comprising a mobile-phase-holding microconduit having a length defined by an upstream terminus and a downstream terminus, and an outlet port located at the downstream terminus, and a mobile phase, contained in the mobile-phase holding microconduit, that exhibits differing concentrations of selected mobile-phase component along the length of the microconduit. The mobile-phase holding microconduit is pressurized to force the mobile phase within the mobile-phase holding microconduit to flow toward the downstream terminus along the length of the microconduit and out of the outlet port. Optionally, at least one inlet port is provided fluid communication with the mobile-phase holding microconduit, wherein the outlet port is located downstream from the at least one inlet port of the mobile-phase holding microconduit. In such a case, a plurality of mobile-phase sources may be provided as well, each containing a mobile phase, wherein each mobile phase contains a different concentration of a selected mobile-phase component. Plugs of mobile phase from the mobile-phase sources are introduced through the at least one inlet port into the mobile-phase holding microconduit such that the plugs are arranged in a predetermined order along the length of the mobile-phase holding conduit.

For any of the embodiments, the mobile-phase holding microconduit may be defined or further defined by a substrate having a microchannel formed in a surface thereof in combination with a cover plate arranged over the substrate surface.

BRIEF DESCRIPTION OF THE DRAWINGS

FIG. 1A illustrates the device in exploded view. FIGS. 1B and 1C schematically illustrate the microfluidic device in loading and operating configurations, respectively.

FIGS. 2A and 2B schematically illustrate the microfluidic device in loading configurations. FIG. 2C schematically illustrates the microfluidic device in an operating configuration.

FIG. 4A illustrates the switching structure in exploded view. FIGS. 4B and 4C schematically illustrate the switching structure in first and second flow path configurations, respectively.

FIG. 5A illustrates the switching structure in a first flow path configuration. FIG. 5B illustrate the switching structure in a second flow path configuration.

DETAILED DESCRIPTION OF THE INVENTION

Figure 1A:
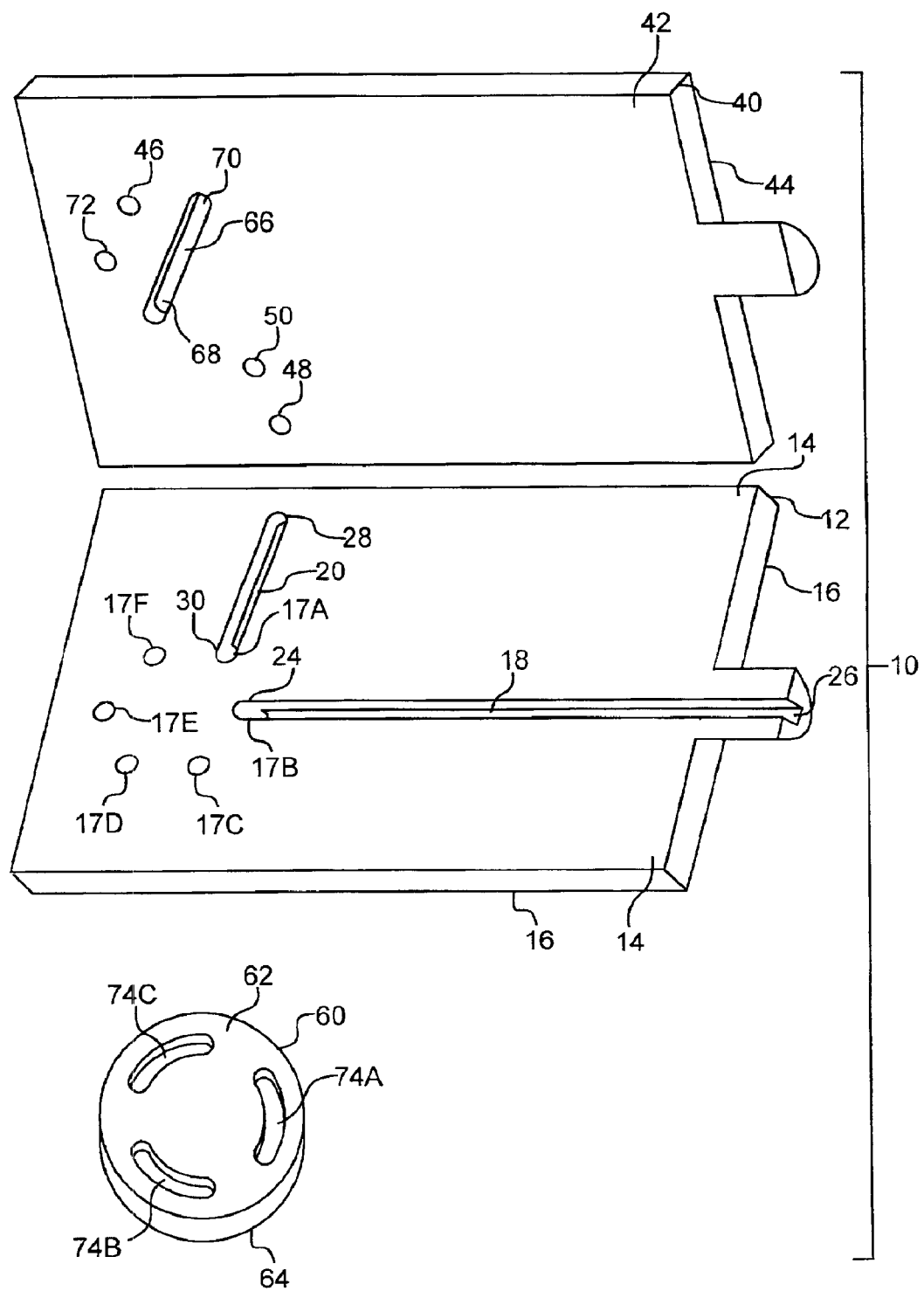
FIGS. 1A–1C, collectively referred to as FIG. 1, illustrate a version of the inventive microfluidic device having an integrated gradient-generation means.

Before the invention is described in detail, it is to be understood that, unless otherwise indicated, this invention is not limited to particular materials, components, or manufacturing processes, as such may vary. It is also to be understood that the terminology used herein is for purposes of describing particular embodiments only, and is not intended to be limiting.

It must be noted that, as used in the specification and the appended claims, the singular forms "a," "an," and "the" include plural referents unless the context clearly dictates otherwise. Thus, for example, reference to "an inlet" includes a plurality of inlets, reference to "a fluid" includes a mixture of fluids, reference to "a cascade" includes a plurality of cascades, and the like.

In this specification and in the claims that follow, reference will be made to a number of terms that shall be defined to have the following meanings:

The term "fluid-tight" is used herein to describe the spatial relationship between two solid surfaces in physical contact such that fluid is prevented from flowing into the interface between the surfaces.

The term "fluid-transporting feature" as used herein refers to an arrangement of solid bodies or portions thereof that direct fluid flow. Fluid-transporting features include, but are not limited to, chambers, reservoirs, conduits, and channels. The term "conduit" as used herein refers to a three-dimensional enclosure formed by one or more walls and having an inlet opening and an outlet opening through which fluid may be transported. The term "channel" is used herein to refer to an open groove or a trench in a surface. A channel in combination with a solid piece over the channel forms a "conduit". A conduit may also be formed from a stencil interposed between two solid surfaces.

The term "microalignment means" is defined herein to refer to any means for ensuring the precise microalignment of microfabricated features in a microfluidic device. Microalignment means can be formed either by laser ablation or by other methods well known in the art that are used to fabricate shaped pieces. Representative microalignment means that can be employed herein include a plurality of appropriately arranged protrusions in component parts, e.g., projections, depressions, grooves, ridges, guides, or the like.

The term "microfluidic device" refers to a device having features of micrometer or submicrometer dimensions, and which can be used in any number of chemical processes involving very small amounts of fluid. Such processes include, but are not limited to, electrophoresis (e.g., capillary electrophoresis or CE), chromatography (e.g., $\mu$LC), screening and diagnostics (e.g., using hybridization or other binding means), and chemical and biochemical synthesis (e.g., DNA amplification as may be conducted using the polymerase chain reaction, or "PCR"), and analysis (e.g., through enzymatic digestion). The features of the microfluidic devices are adapted to the particular use intended. For example, microfluidic devices that are used in separation processes such as chromatography contain microchannels (termed herein as "microconduits" when they are enclosed, i.e., when the cover plate is in place on the microchannel-containing substrate surface) on the order of 1 $\mu$m to 200 $\mu$m in diameter, typically 10 $\mu$m to 75 $\mu$m in diameter, and approximately 0.1 to 50 cm in length. For microfluidic devices that are used in generating or holding a gradient-containing mobile phase, conduits associated with gradient-generation means may have a volume of about 1 nL to about 100 $\mu$L, typically about 10 nL to 20 $\mu$L.

The term "mobile phase" as used herein refers to any fluid capable of movement under a motive force. Although the term "mobile phase" is typically used in the context of separation processes such as chromatography, the term is not limited to such processes.

"Optional" or "optionally" as used herein means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The invention generally relates to a microfluidic device for separating the components of a fluid sample, wherein the microfluidic device is formed from a substrate having a microchannel in a surface thereof and a cover plate arranged over the substrate surface. The cover plate, in combination with the microchannel, defines a separation conduit for separating the components of a fluid sample according to a specific component property; the separation conduit has an inlet port and an outlet port. The microfluidic device also includes an integrated gradient-generation means for generating a gradient of a selected mobile-phase component in a mobile phase. The integrated gradient-generation means is arranged to allow the mobile phase from the gradient-generation means to be transported through the inlet port into the separation conduit and out of the outlet port. Typically, though not necessarily, the integrated gradient-generation means is formed at least in part within the substrate and/or in the cover plate.

Typically, the integrated gradient-generation means includes a mobile-phase holding conduit having a length defined by an upstream terminus and a downstream terminus. A plurality of inlet ports is arranged along the length of the mobile-phase holding conduit, and an outlet port is located downstream from the inlet ports of the mobile-phase holding conduit. An introduction means is provided for introducing the mobile phase from the mobile-phase holding conduit through its outlet port and into the inlet port of the separation conduit. This gradient-generation means, as well as variations thereof, is further discussed below.

FIG. 1 illustrates an embodiment of the inventive microfluidic device having an integrated gradient-generation means as described above, in combination with a separation column for liquid chromatography. As with all figures referenced herein, in which like parts are referenced by like numerals, FIG. 1 is not necessarily to scale, and certain dimensions may be exaggerated for clarity of presentation. As illustrated in FIG. 1, the microfluidic device 10 includes a substrate 12 comprising first and second substantially planar opposing surfaces indicated at 14 and 16, respectively, and is comprised of a material that is substantially inert with respect to fluids that will be transported through the microfluidic device. The substrate 12 has a first fluid-transporting feature in the form of a separation microchannel 18 and a second fluid-transporting feature in the form of a mobile-phase holding microchannel 20, each microchannel located in the first planar surface 14. The separation microchannel 18 represents a portion of a separation conduit 19, and the mobile-phase holding microchannel 20 represents a portion of the mobile-phase holding conduit 21, as discussed below. The separation microchannel 18 has a sample inlet terminus 24 at an upstream end and a sample outlet terminus 26 at the opposing end. As shown in FIG. 1, the sample outlet terminus 26 is located at a protrusion of the otherwise rectangular substrate 12. Similarly, the mobile-phase holding microchannel 20 has a length defined by an upstream terminus 28 and a downstream terminus 30.

The substrate 12 has six conduits, indicated at 17A, 17B, 17C, 17D, 17E and 17F that extend through surfaces 14 and 16 and that represent the vertices of an equilateral hexagon. Conduit 17A is located at the downstream terminus 30 of the mobile-phase holding microchannel 20. Conduit 17B is located at the sample inlet terminus 28 of the separation microchannel 18.

The microfluidic device 10 also includes a cover plate 40 that is complementarily shaped with respect to the substrate 12 and has first and second substantially planar opposing surfaces indicated at 42 and 44, respectively. The cover plate 40 can be comprised of any suitable material for forming the substrate 12 as described below. The contact surface 42 of the cover plate 40 is capable of interfacing closely with the contact surface 14 of the substrate 12 to achieve fluid-tight contact between the surfaces. The cover plate 40 may include a variety of features. As shown, mobile-phase inlet ports 48 and 50 are provided as a cylindrical conduit extending through the cover plate 40 in a direction orthogonal to the cover plate contact surface 42 to result in fluid communication between surfaces 42 and 44. Similarly, sample inlet port 72 and sample outlet port 46 are provided as conduits extending from surface 42 to surface 44. A sample introduction channel 66 having termini 68 and 70 is located on contact surface 42.

The cover plate 40 is substantially immobilized over the substrate contact surface 14, and the cover plate contact surface 42 in combination with the separation microchannel 18 defines a sample conduit 19 for conveying the sample. Similarly, the cover plate 40, in combination with the mobile-phase holding channel 20, defines a mobile-phase holding conduit 21. In addition, the sample introduction channel 66 combined with the substrate contact surface 14 forms sample introduction conduit 67. Because the contact surfaces of the cover plate and the substrate are in fluid-tight contact, the separation conduit 19, the mobile-phase holding conduit 21, and sample introduction conduit 67 are all fluid-tight as well. Mobile-phase inlet port 48 is located over the upstream terminus 28 of the mobile-phase holding-channel 20 and mobile phase inlet port 50 is located over the mobile-phase holding channel 20 at approximately the midpoint between its termini 28 and 30. Sample inlet port 72 and sample outlet port 46 are aligned with conduits 17E and 17D, respectively. Termini 68 and 70 of sample introduction channel 66 are aligned with conduits 17F and 17C, respectively.

A switching plate 60 is provided as an integrated means for sample introduction. The switching plate also serves to provide controllable communication between the mobile-phase holding conduit 21, the sample introduction conduit 67, and the separation conduit 19. This switching plate 60 is similar to that described in U.S. Ser. Nos. 09/908,292 and 09/908,231. As depicted in FIG. 1A, the switching plate 60 has a substantially planar and circular contact surface 62 and an opposing surface 64. As shown, the surfaces 62 and 64 are generally congruent. Three curved fluid-transporting channels, indicated at 74A, 74B and 74C, are each located on contact surface 62. The three fluid-transporting channels lie along a circle having a diameter equal to the length of sample introduction channel 66. Each fluid-transporting channel has two termini such that each terminus represents a vertex of an equilateral hexagon that is congruent with the equilateral hexagon formed by the through conduits 17A–17F of the substrate 12. The switching plate contact surface 62 may be placed in slidable and fluid-tight contact with substrate surface 16. As a result, the fluid-transporting channels, 74A, 74B, and 74C, in combination with substrate surface 16, form three curved conduits, 75A, 75B, and 75C, respectively.

Figure 1B:
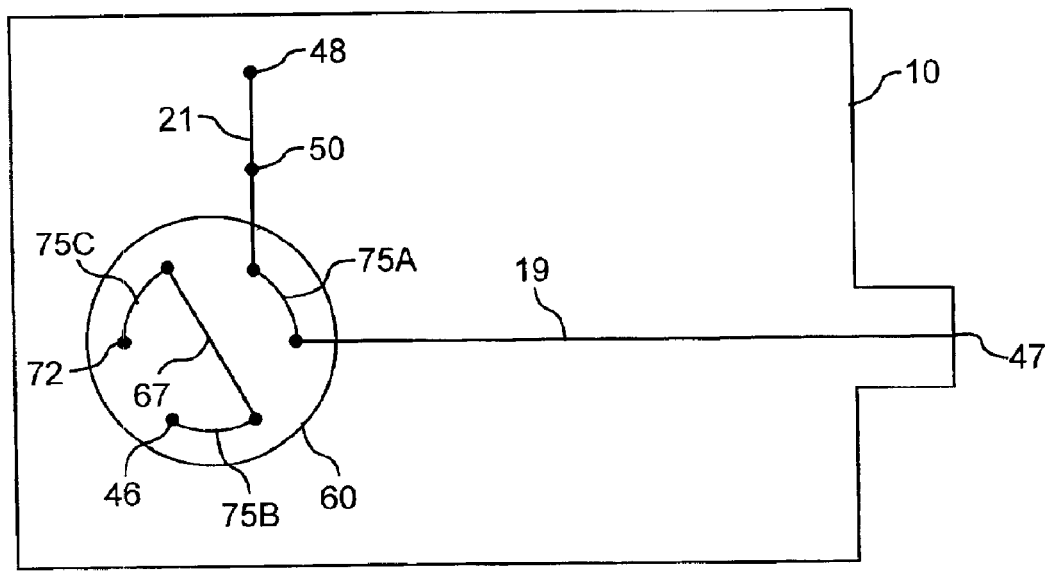
Figure 1C:
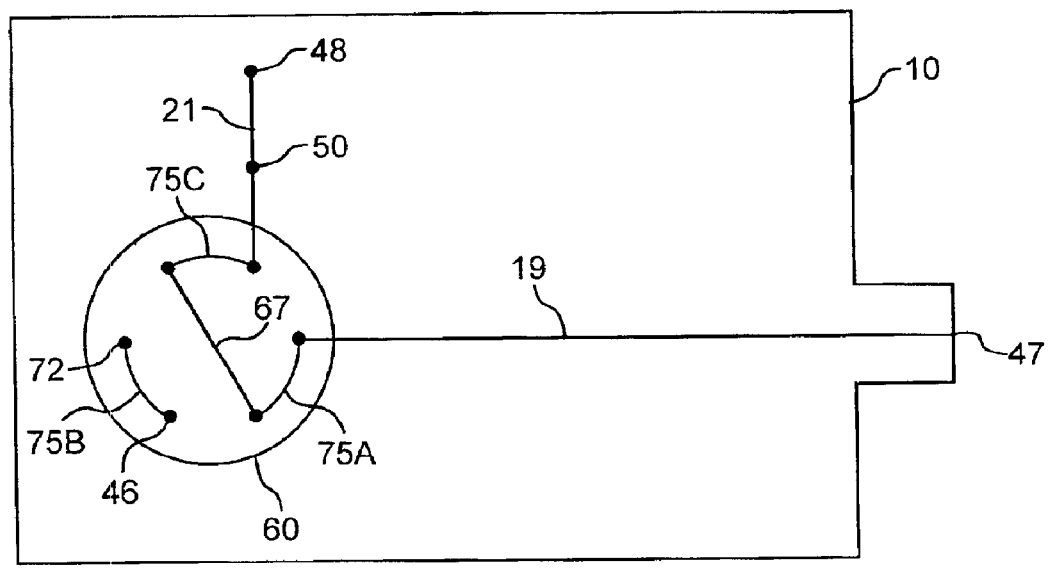

Depending on the relative orientation of the switching plate and the substrate two possible flow paths configurations can be created. As shown in FIG. 1B, the first flow path configuration allows a sample fluid to be introduced into the microfluidic device through sample inlet port 72 through conduit 75C, the sample introduction conduit 67 and conduit 75B. The sample fluid may then exit the microfluidic device 10 through sample outlet port 46. By rotating the switching plate 60 60° about its center, a second flow path configuration results, as shown in FIG. 1C. The second flow path configuration positions the sample introduction conduit 67 in a flow path between the mobile-phase holding conduit 21 and the separation conduit 19. As a result, a flow path is formed from mobile-phase holding conduit 21 through conduit 75C, sample introduction conduit 67, conduit 75A, and separation conduit 19.

The microfluidic device may be employed in a method for separating the components of a fluid sample in a manner similar to that of a simple capillary liquid chromatographic apparatus. The integrated gradient-generation means may be used to generate the gradient of the selected mobile-phase component in the mobile phase by providing the inlet ports 48 and 50 of the mobile-phase holding conduit fluid communication with a source of mobile phase (not shown) such that mobile phase containing differing concentrations of the selected mobile-phase component may be introduced into each inlet port. Thus, once filled with mobile phases from the inlet ports 48 and 50, the upstream portion of the mobile-phase holding conduit 21 may contain a different concentration of the selected mobile-phase component than the downstream portion. Given sufficient time for diffusion to occur, the mobile-phase holding conduit 21 along its length may contain mobile phase that exhibits a smooth gradient of the selected mobile-phase component. By proper choice of the concentration of the selected mobile-phase component in a mobile-phase source, the gradient of the selected mobile-phase component may increase or decrease along the length of the mobile-phase holding conduit 21 in a downstream direction.

In addition, as shown in FIG. 1B, fluid sample is introduced into the sample inlet port 72 to fill the sample introduction conduit 67. Typically, the combination of the sample introduction conduit 67 and conduit 75C holds a predetermined volume (i.e., a plug) of sample therein. Once a desired gradient is formed in the mobile-phase holding conduit 21, the switching plate 60, as indicated in FIG. 1C is slidably rotated to provide communication between the mobile-phase holding conduit 21 and the separation conduit 19. A pressurizing means (not shown) provides a motive force to deliver the mobile phase contained in the mobile-phase holding conduit 21 through the sample introduction conduit 67 and into the separation conduit 19. As a result, the fluid sample contained within the sample introduction conduit 67 is conveyed though the separation conduit 19. Typically, separation within the separation conduit 19 is carried out using a mobile-phase flow rate of no more than about 1 μL/min. However, flow rates of about 0.01 μL/min to about 10 μL/min may be employed, with flow rates of about 0.1 μL/min to about 2 μL/min preferred. The fluid sample is then separated into sample components according to a specific component property and emerges from an outlet port 47 at the terminus 26 of the separation conduit. The outlet port 47 may be interfaced with a collector, such as a sample vial, plate, or capillary. The collector may serve as a storage device or represent an intermediary to another device that uses and/or analyzes collected sample fractions. Alternatively, an analytical device such as a mass spectrometer may be directly or indirectly interfaced with the outlet port 47 for fraction analysis.

Figure 2A:
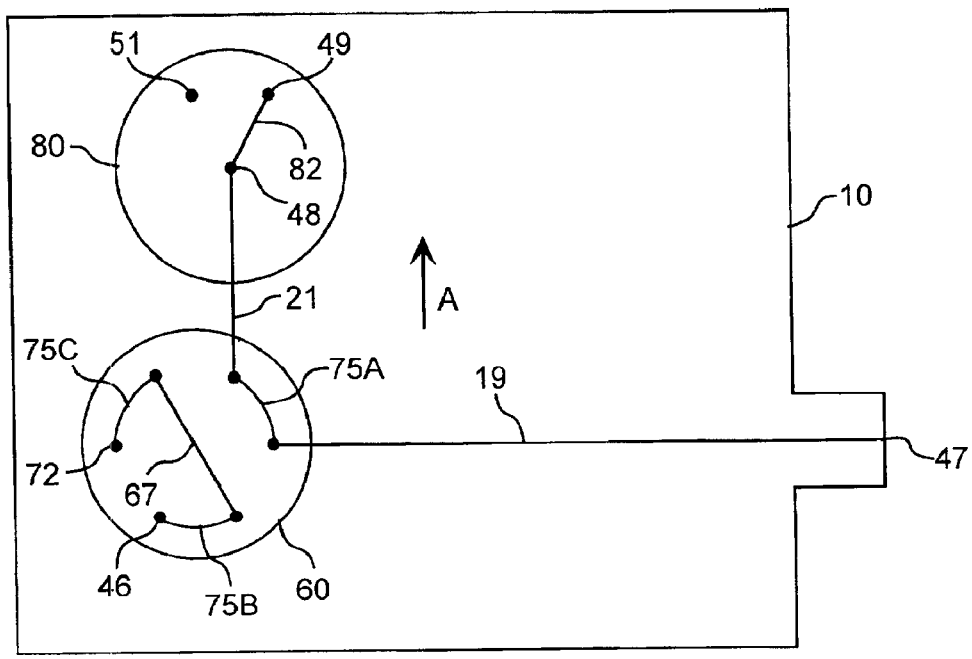
FIGS. 2A–2C, collectively referred to as FIG. 2, illustrate a version of the inventive microfluidic device similar to that illustrated in FIG. 1, but having a different integrated gradient-generation means.
Figure 2B:
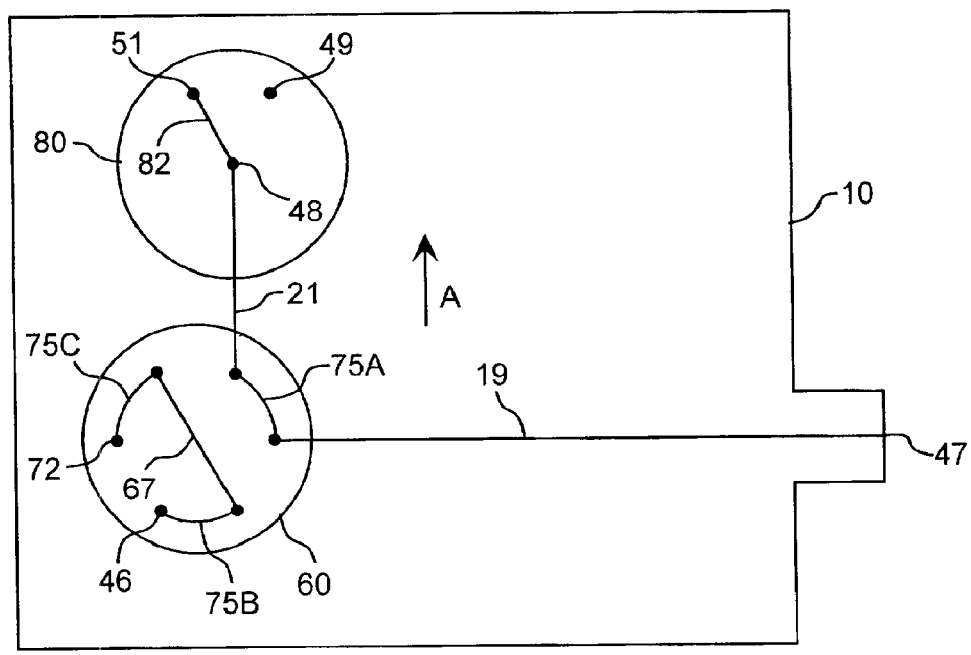

Although a plurality of inlet ports is depicted as arranged along the length of the mobile-phase holding conduit in FIG. 1, this configuration is not a necessity. FIG. 2 illustrates another version of the inventive microfluidic device 10, similar to that depicted in FIG. 1 except that the mobile-phase holding conduit 21 of the integrated gradient-generation means has a single inlet port 48 located at its upstream terminus rather than a plurality of inlet ports arranged along the length of the mobile-phase holding conduit. In addition, the integrated gradient-generation means includes an additional switching plate 80 that contains a mobile-phase introduction conduit 82 to provide the mobile-phase holding conduit 21 with alternating fluid communication with a plurality of mobile-phase sources indicated at 49 and 51, and each source containing a different concentration of the selected mobile-phase component for gradient formation. As shown in FIG. 2A, a first mobile-phase source 49 is provided fluid communication through the mobile-phase introduction conduit 82 with the mobile-phase holding conduit 21 of the microfluidic device 10, while a second mobile-phase source 51 is fluidly isolated from the mobile-phase holding conduit 21. FIG. 2B illustrates that the second mobile-phase source 51 may be provided fluid communication with the mobile-phase holding conduit 21 through the mobile-phase introduction conduit 82 while the first mobile-phase source 49 is fluidly isolated from the mobile-phase holding conduit 21.

Figure 2C:
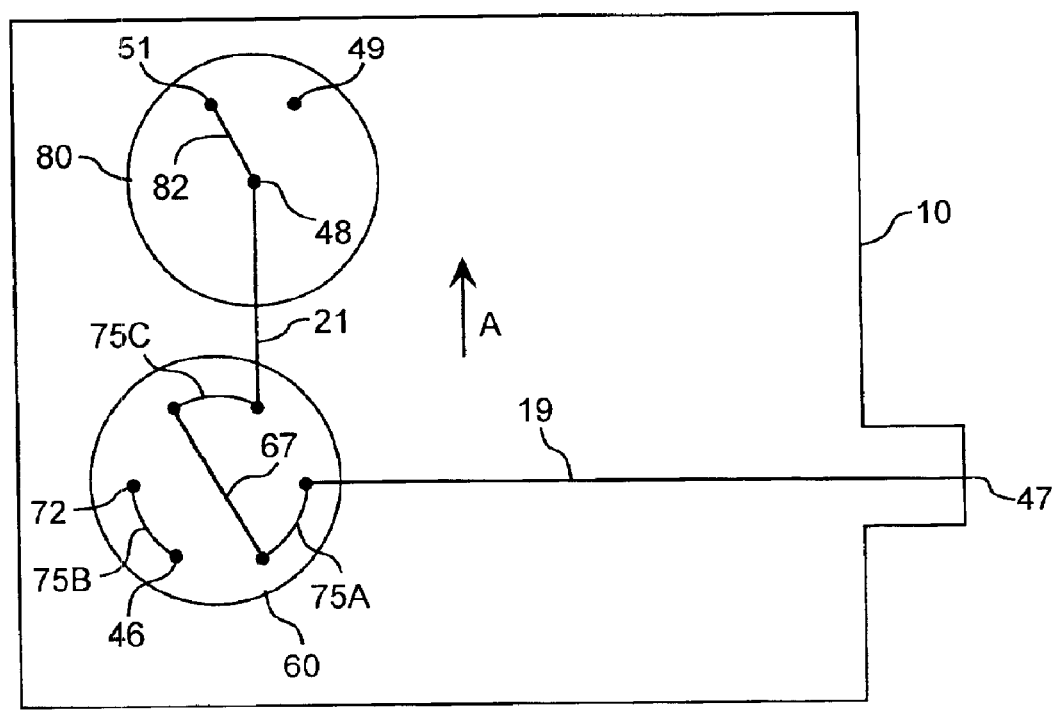

By providing the mobile-phase holding conduit 21 with alternating fluid communication in a predetermined loading sequence with mobile-phase sources 49 and 51, the mobile-phase holding conduit 21 may be filled with a mobile phase having a concentration profile of the selected mobile-phase component along the length of the mobile-phase holding conduit 21. As before, given sufficient time for diffusion to occur, the mobile phase along the length of the mobile-phase holding conduit 21 may come to contain a smooth gradient of the selected mobile-phase component. For example, the first mobile-phase source 49 may contain the selected mobile-phase component in a pure form, and the second mobile-phase source 51 may contain a fluid that does not contain the selected mobile-phase component. Plugs of increasing volume of fluid from the first mobile-phase source 49 are alternatingly introduced through inlet port 48 into the mobile-phase holding conduit 21 with plugs of identical volumes of fluid from the second mobile-phase source 51. Such alternating introduction can be effected through a number of valve actuation technologies including those that employ computer-aided control. After sufficient time has elapsed to allow for diffusion of the selected mobile-phase component, the mobile-phase holding conduit 21 will exhibit a smooth and increasing gradient of the selected mobile-phase component along its length in an upstream direction, as indicated by arrow A. Once the desired gradient is formed in the mobile-phase holding conduit 21, the mobile phase may be delivered into a separation conduit 19 in order to separate the components of a sample, as illustrated in FIG. 2C.

In another embodiment, the invention relates to a microfluidic device for separating the components of a fluid sample. The microfluidic device comprises a gradient-generation means, a separation conduit for separating the components of a fluid sample according to a specific component property, as well as a means for introducing mobile phase from the gradient-generation means. The gradient-generation means is constructed from a substrate and a cover plate. A microchannel is formed in a surface of the substrate and has an upstream terminus and a downstream terminus. The cover plate is arranged over the substrate surface and, in combination with the microchannel, forms a mobile-phase holding conduit having a length defined by the upstream terminus and the downstream terminus. A plurality of inlet ports is arranged along the length of the mobile-phase holding conduit, and an outlet port is located downstream from the inlet ports of the mobile-phase holding conduit. Each of the inlet ports may fluidly communicate with the same or different sources of mobile phase as described below.

Generally, increasing the number of inlet ports for the mobile-phase holding conduit will provide greater control in gradient generation. Thus, the mobile-phase holding conduit may have any number of inlet ports greater than two. It is generally preferred that the inlet ports be evenly spaced along the length of the mobile-phase holding conduit, particularly when the mobile-phase holding conduit represents a gradient-generation means that comprises a cascade of conduits that split and mix streams of liquids (for example, water and methanol). A similar cascade is generally described in Whitesides et al. (2001), "Flexible Methods for Microfluidics," *Physics Today* 52(6):42–47. As described in Whitesides et al., the cascade may be employed in techniques that involve the immobilization of cells in a pattern on a surface of a microfluidic device wherein the cells are exposed to fluids containing appropriate reagents. Splitting of streams of liquid occurs at T-junctions between mixing channels and distribution channels. At steady state, the ultimate result of this splitting and mixing is the generation of a stepwise concentration gradient. However, the fluids may be delivered as a linear gradient of an appropriate reagent, e.g., a dye gradient, formed by diffuse mixing through a network of microchannels.

Figure 3:
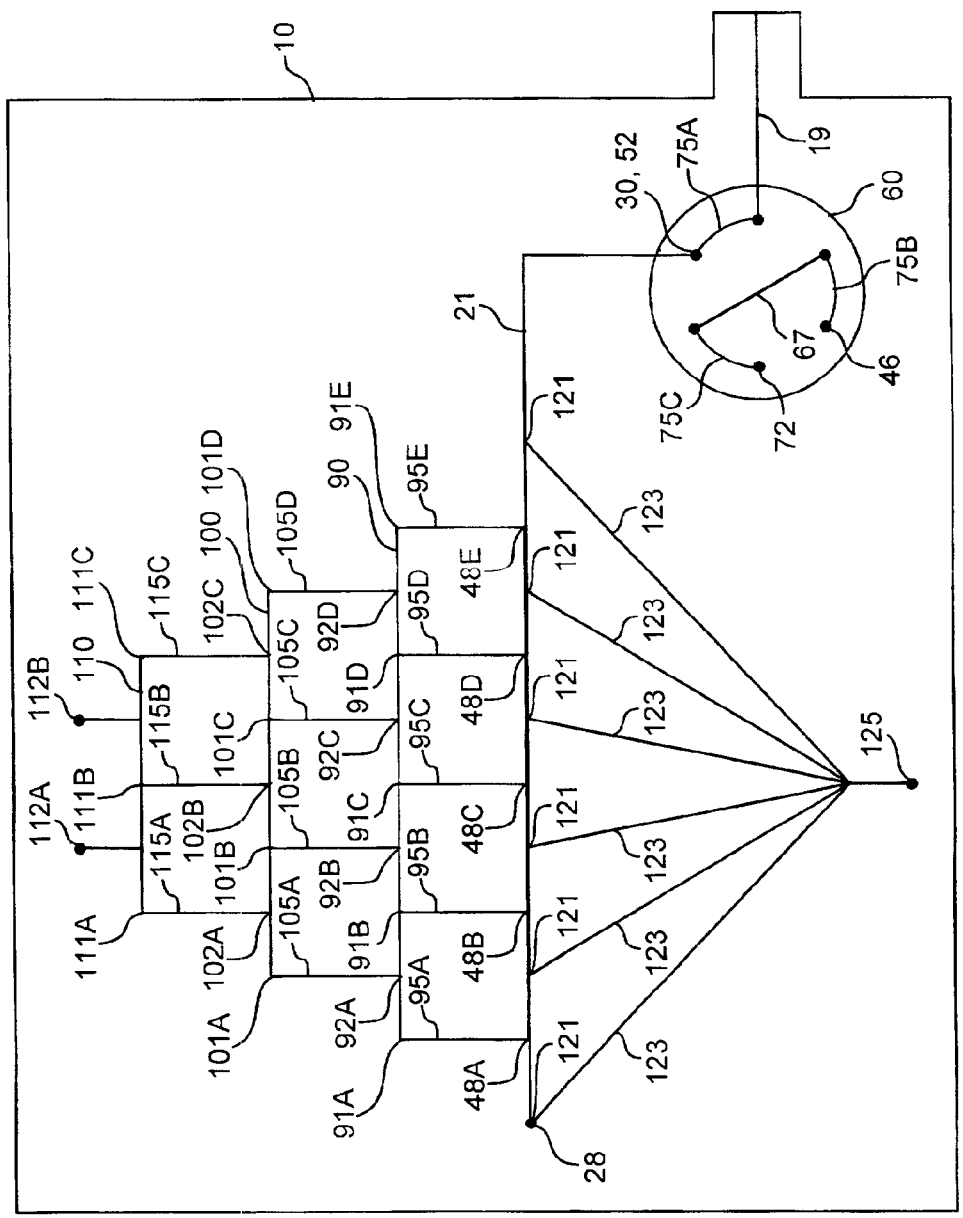
FIG. 3 schematically illustrates a microfluidic device for separating the components of a fluid sample, wherein the microfluidic device contains a cascade of microchannels suitable for generating a smooth gradient in a mobile phase.

FIG. 3 illustrates an example of such a cascade on a microfluidic device 10 similar to that illustrated in FIG. 1. The cascade is depicted as a collection of microconduits formed from the combination of microchannels on a substrate and a cover plate, although this is not a necessity. The gradient-generation means includes a mobile-phase holding conduit 21 having an upstream terminus 28 and a downstream terminus 30. Five inlet ports, indicated at 48A, 48B, 48C, 48D, and 48E, are evenly spaced along its length. An outlet port 52 is located at the downstream terminus 30. As shown, no inlet port is located at either terminus of the mobile-phase holding conduit. Three distribution conduits, indicated at 90, 100, and 110, are arranged in parallel disposition in successively increasing distances to the mobile-phase holding conduit 21. Each successive distribution conduit from the mobile-phase holding conduit 21 has the same number of outlet ports as the preceding conduit. However, each successive distribution conduit from the mobile-phase holding conduit 21 has one fewer inlet port than the preceding conduit. Thus, distribution conduit 90 has five outlet ports 91A, 91B, 91C, 91D, and 91E, and four inlet ports 92A, 92B, 92C, and 92D; distribution conduit 100 has four outlet ports 101A, 101B, 101C, and 101D, and three inlet ports 102A, 102B, and 102C; and distribution conduit 110 has three outlet ports 111A, 111B, and 111C, and two inlet ports 112A and 112B. Each outlet port of each distribution conduit fluidly communicates via a mixing conduit with an inlet port of a successive conduit. Each inlet port of the distribution conduits is located between two outlet ports of the same distribution conduit.

The gradient-generation process is now described. Turning to distribution conduit 110, inlet ports 112A and 112B are provided fluid communication with two sources of mobile phase, each holding a different concentration of the selected mobile-phase component for which a gradient is to be generated. Typically, one of the mobile-phase sources (in this case, the mobile-phase source communicating with inlet port 112A, holds a first mobile phase of the selected mobile-phase component while the other mobile-phase source (in this case, the mobile-phase source communicating with inlet port 112B holds a second mobile phase that contains another selected mobile-phase component altogether. When mobile phases from the mobile-phase sources are introduced into distribution conduit 110, the first and second mobile phases will preferentially fill the portion of the conduit closest to their associated inlet ports. Thus, the first mobile phase will preferentially fill the portion of distribution conduit 110 closer to outlet port 111A, and the second mobile phase will preferentially fill the portion of the distribution conduit 110 closer to terminus 111C. Mixing channel 115A will contain only the first mobile phase, and mixing channel 115C will contain only the second mobile phase.

However, as mixing channel 115B lies between inlet ports 112A and 112B, mixing channel 115B will contain both mobile phases. Thus, the inlets along distribution conduit 100 will provide mobile phases containing increasing concentrations of the selected mobile phase along the length of the distribution conduit from outlet 101A to outlet 101D. It should be evident that this mixing and redistribution process is repeated for each of the distribution conduits to result in the generation of a smooth gradient in the mobile-phase holding conduit 21. Optionally, a plurality of waste/exhaust ports indicated at 121 is provided in fluid communication with mobile-phase holding conduit to allow any air or other fluid contained in the mobile-phase holding conduit to be displaced during the gradient generation process. As shown, the waste/exhaust ports may fluidly communicate with each other through converging conduits 123 at gradient outlet 125. Once a gradient is generated in the mobile-phase holding conduit 21, a pressurizing means (not shown) may be employed to provide a motive force to deliver the mobile phase contained in the mobile-phase holding conduit into the separation conduit 19 to carry out separation processes as described above and elsewhere herein.

In order to ensure the proper formation of a smooth gradient, the following considerations should be addressed. First, the residence time of the fluids in the mixing conduits should be sufficiently long to ensure near-complete mixing. Second, the flow resistance of the mixing conduits should be significantly greater than the flow resistance of the distribution and holding conduits. This minimizes backflow into the mixing conduits as the concentration gradient is pumped out of the holding conduit. Third, the characteristic length of the cascade should be long enough to prevent destruction of the gradient by complete diffuse mixing while it is waiting to be pumped into the separations. However, as discussed above, some degree of diffusion may be beneficial in smoothing of the concentration steps. Finally, additional design considerations, such as tailoring of the dimensions of each individual mixing conduit, can be made to account for differences in viscosity between the two mobile phases. Although mobile phases having different viscosities may be used, the following analyses assume that the mobile phases have the same viscosity and that the conduits are formed from conduits.

With respect to residence time, a two-dimensional order of magnitude analysis assuming a uniform flow with no entrance length effects and no reflections at the conduit, yields the following dependence for the characteristic mixing length, $L_m$:

$$L_m \sim a^2 \bar{u}/2D = a \cdot Pe/2 \qquad (1)$$

where a is the half-width of the conduit, $\bar{u}$ is the average flow velocity in the conduit, D is the diffusion coefficient of the diffusing species, and Pe is the Peclet number (which expresses the ratio of convective to diffusive transport).

The gradient-generation cascade is designed such that the flow resistance of the mixing conduits is much greater than the flow resistance of the distribution and holding conduits. In this case, the flow resistance of the distribution conduits can be neglected, resulting in an equal distribution of the total volumetric flow rate, Q, among the mixing conduits. Each mixing conduit would then support a flow rate equal to the total flow rate, Q, divided by the number of conduits in that stage of the cascade. Thus, the highest flow rates are encountered at the first mixing conduits, resulting in the following order of magnitude estimate for the characteristic mixing length of conduits with a cross-sectional area given by 2a*h (twice the half-width, multiplied by the depth of the conduit):

$$L_m \sim aQ/12Dh \qquad (2)$$

Then, for example, the characteristic mixing length for a species with a diffusion coefficient of $1.28 \times 10^{-5}$ cm$^2$/s, a conduit with a depth h=a, and a total volumetric flow rate of 300 nL/min, would be on the order of 330 $\mu$m. In summary, the mixing conduits should be at least three times the characteristic mixing length, which is directly proportional to the total volumetric flow rate and inversely proportional to the product of the diffusion coefficient and the aspect ratio, h/a, of the conduit. For a given diffusing species, we can reduce the mixing length by lowering the total flow rate and aspect ratio of the conduit.

A more detailed analytical solution for the two-dimensional problem, including wall reflections, is given in Jeon et al. (2000), "Generation of solution and surface gradients using microfluidic systems," *Langmuir* 16:8311–8316; and in Crank, *The Mathematics of Diffusion*, 2$^{nd}$ Ed., Oxford University Press, Oxford, 1975, pp. 16. The Netflow Module of FlumeCAD (Coventor, Inc., Cary, N.C.) has also been employed to calculate the mixing length for the conditions listed above. According to these simulations, near-complete mixing occurs at approximately 1000 mm into the conduit, or approximately three characteristic mixing lengths away from the entrance to the conduit.

With respect to the flow resistance of the mixing conduits in relationship to the flow resistance of the distribution and holding conduits, the equivalent flow resistance of a flow conduit supporting fully developed laminar flow can be approximated by:

$$R = |\Delta p/Q| = 128 \, \mu L / \pi d_h^4 \qquad (3)$$

where $\Delta p$ is the change in pressure, $\mu$ is the viscosity of the fluid, L is the length of the conduit, and $d_h$ is the hydraulic diameter of the conduit. The hydraulic diameter is defined as four times the cross-sectional area of the conduit, divided by the perimeter of the cross section. The depth, h, of a shallow conduit dominates in the computation of the hydraulic diameter.

The requirement that the flow resistance of the mixing conduits be much greater than the flow resistance of the distribution and holding conduits can be expressed as:

$$(d_h)_{dist}^4 / L_{dist} \gg (d_h)_{mix}^4 / L_{mix} \qquad (4)$$

The characteristic length of the cascade, A, and the diffusion coefficient of the diffusing species are the parameters that determine the stability of the gradient in the holding conduit as the gradient is waiting to be introduced into the separation conduit. From a simulation of the concentration of water and methanol in the holding conduit as a function of time for a conduit 200 $\mu$m wide, a characteristic length of 5000 $\mu$m, and nine gradient steps (i.e., a gradient cascade of order 9), a smooth gradient is formed after about one minute and is stable for at least 50 minutes.

Thus, the invention also relates to a microfluidic device having an integrated mobile-phase source. The microfluidic device comprises a substrate having a microchannel formed in a surface thereof and a cover plate arranged over the substrate surface. The cover plate in combination with the microchannel defines a separation conduit for separating the components of a fluid sample according to a specific component property and has an inlet port and an outlet port. An integrated mobile-phase source is provided, which comprises a microconduit having a length defined by an upstream terminus and a downstream terminus. The microconduit contains a mobile phase that exhibits a gradient of a selected mobile-phase component along the length of the microconduit. The integrated mobile-phase source is arranged to allow the mobile phase to be transported through the inlet port into the separation conduit and out of the outlet port.

Through proper microfluidic device design and construction, it is now possible to use no more than about 100 $\mu$L of fluid to produce a mobile phase containing a gradient of the selected mobile-phase component to carry out gradient chromatography. Preferably, no more than about 50 $\mu$L of fluid is used to produce the gradient-containing mobile phase. Optimally, no more than about 10 $\mu$L of fluid is used produce the gradient-containing mobile phase. The gradient-containing mobile phase is used to convey a fluid sample through the separation conduit, thereby separating the components of the fluid sample.

From the above, it is evident that the invention, in addition to providing a device for separating the components of a fluid, also provides a microfluidic device for producing a flow of mobile phase. The device comprises a mobile-phase source and a pressurizing means. The mobile-phase source comprises a mobile-phase holding microconduit having a length defined by an upstream terminus and a downstream terminus, and an outlet port located at the downstream terminus, and a mobile phase, contained in the mobile-phase holding microconduit, that exhibits differing concentrations of selected mobile-phase component along the length of the mobile-phase holding microconduit. The pressurizing means allows for the pressurization of the microconduit to force the mobile phase within the microconduit to flow toward the downstream terminus along the length of the microconduit and out the outlet port. Any number of pressurizing means known in the art may be used and include, for example, syringes, pumps, pressurized gases, etc. Although electrokinetic forces may be used as well, they are not preferred. Such forces are dependent on the concentration of the mobile phase and the electrokinetic mobility will vary along any flow path exhibiting a gradient, leading to difficulties in control over mobile phase movement.

The mobile-phase as described above, may be produced by any of a number of different techniques, described herein with references to FIGS. 1–3, in the context of chemical separation using a gradient-containing mobile phase. However, mobile phases may also be employed in the context of fields other than chemical separation. In addition, it should be apparent the gradient-generation means as described above may be adapted to produce a mobile phase that contains different concentrations of a selected mobile-phase component at different locations within a mobile phase.

Thus, the invention also generally relates to a microfluidic device for producing a flow of mobile phase, wherein a producing means is provided to generate a gradient of a selected mobile-phase component in a mobile phase, to produce a mobile phase exhibiting different concentrations of a selected mobile-phase component in different locations within the mobile phase, or both. Such a producing means typically comprises a mobile-phase-holding microconduit having a length defined by an upstream terminus and a downstream terminus, an outlet port located at the downstream terminus, and at least one inlet port in fluid communication with the mobile-phase holding microconduit upstream from the outlet port. A plurality of mobile-phase sources are also provided, wherein each source contains a mobile phase having a different concentration of a selected mobile-phase component. An introduction means introduces plugs of mobile phase from the mobile-phase sources through the at least one inlet port into the mobile-phase holding conduit such that the plugs are arranged in a predetermined order along the length of the mobile-phase holding conduit. As illustrated in FIG. 2, the introduction means may be formed at least in part by a switching structure.

Figure 4A:
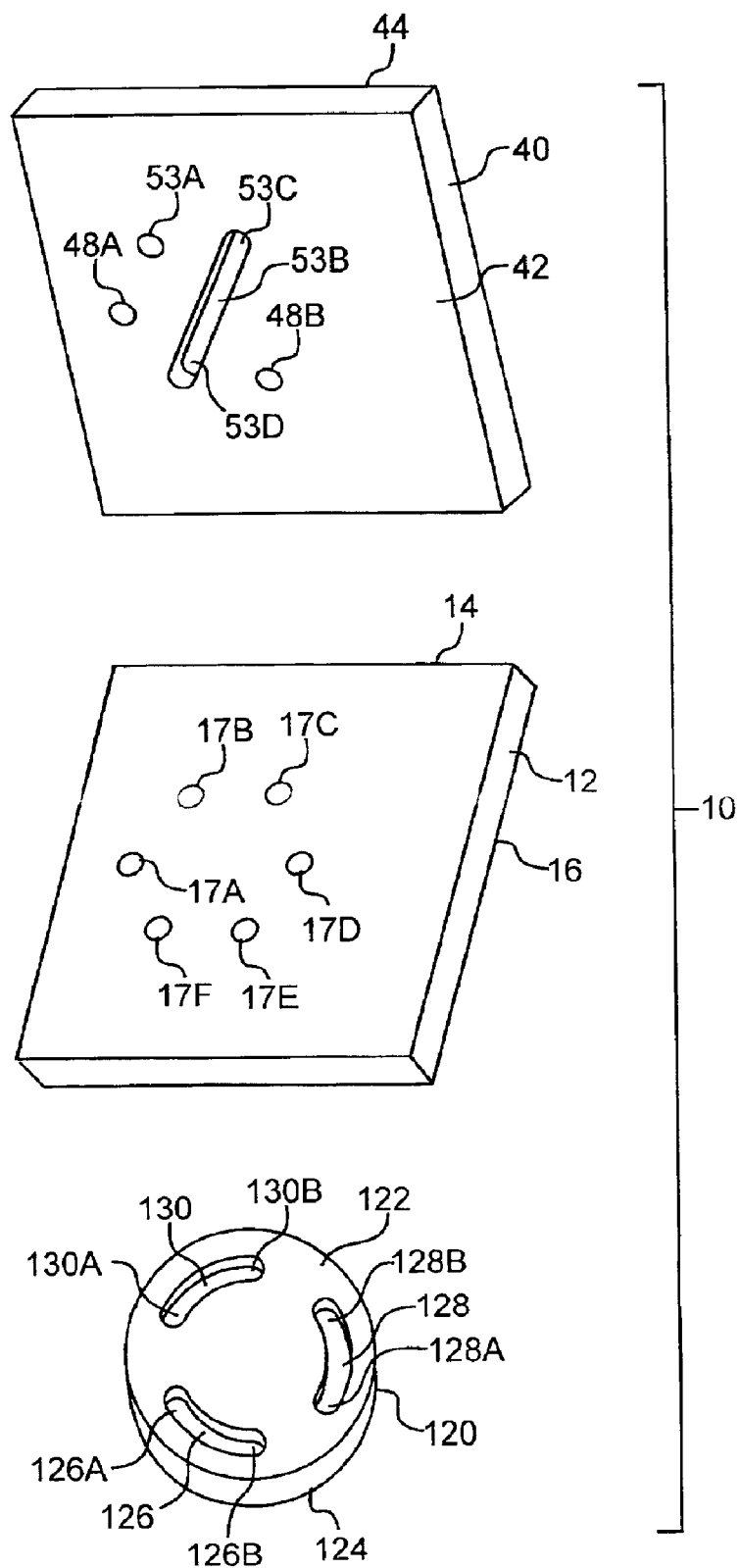
FIGS. 4A–4C, collectively referred to as FIG. 4, illustrate a switching structure employs rotational motion to controllably introduce, through a conduit, a plug of a first mobile phase followed by a second mobile phase.

FIGS. 4 and 5 illustrate two additional switching structures that may be employed as an introduction means. FIG. 4 illustrates a microfluidic switching structure similar to that described in U.S. Ser. No. 09/908,231. The switching structure employs rotational motion to controllably introduce a plug of a mobile phase. As illustrated in FIG. 4A, the switching structure 10 includes a substrate 12 comprising first and second substantially planar opposing surfaces indicated at 14 and 16, respectively. The substrate 12 has six conduits, indicated at 17A, 17B, 17C, 17D, 17E and 17F that extend through surfaces 14 and 16 and that represent the vertices of an equilateral hexagon.

The switching structure 10 also includes a cover plate 40 that is complementarily shaped with respect to the substrate 12 and has first and second substantially planar opposing surfaces indicated at 42 and 44, respectively. The contact surface 42 of the cover plate 40 is capable of interfacing closely with the contact surface 14 of the substrate 12 to achieve fluid-tight contact between the surfaces. The cover plate 40 is substantially immobilized over the substrate contact surface 14. The cover plate 40 includes a variety of features. As shown, a first cover plate conduit 48A is provided extending through the cover plate in a direction orthogonal to the cover plate contact surface 42 to provide communication between surfaces 42 and 44. The first cover plate conduit 48A is arranged to communicate with the conduit 17A of the substrate 12 and enables passage of first mobile phase from a first mobile phase source (not shown) through conduit 17A to communicate with switching plate 120 as discussed below. Two additional cylindrical conduits, indicated at 53A and 48B are provided fluid communication with conduits 17F and 17C, respectively.

A linear channel 53B having two termini, indicated at 53C and 53D, is located in contact surface 42. The termini 53C and 53D fluidly communicate with conduits 17E and 17B, respectively. The termini 53C and 53D in combination with conduits 48A, 48B and 53A represent five of six vertices of an equilateral hexagon. Accordingly, each of the conduits is located the same distance from the center point of the channel 53B. As discussed above, the cover plate 40 is substantially immobilized over the substrate contact surface 14. As a result, substrate surface 14 in combination with channel 53B forms a conduit 55, which serves as a plug holding chamber, discussed below. Alternatively, the linear channel 53B may be provided on substrate surface 14. In such a case, termini 53C and 53D would coincide in location with conduits 17B and 17E, respectively.

As shown in FIG. 4A, the switching plate 120 has a substantially planar and circular contact surface 122 and an opposing surface 124. Three curved fluid-transporting channels, indicated at 126, 128 and 130, are each located on contact surface 122. The three fluid-transporting channels lie along a circle having a diameter equal to the length of channel 53B. Each fluid-transporting channel has two termini: termini 126A and 126B are associated with channel 126, termini 128A and 128B are associated with channel 128, and termini 130A and 130B are associated with channel 130. The switching plate contact surface 122 may be placed in slidable and fluid-tight contact with substrate surface 16. As a result, the fluid-transporting channels, 126, 128 and 130, in combination with substrate surface 16, form three curved conduits, 126C, 128C, 130C, respectively.

Figure 4B:
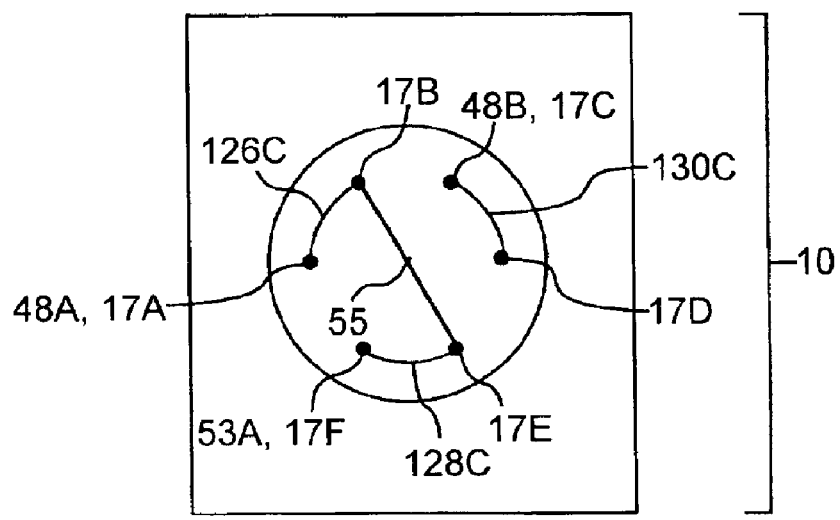
Figure 4C:
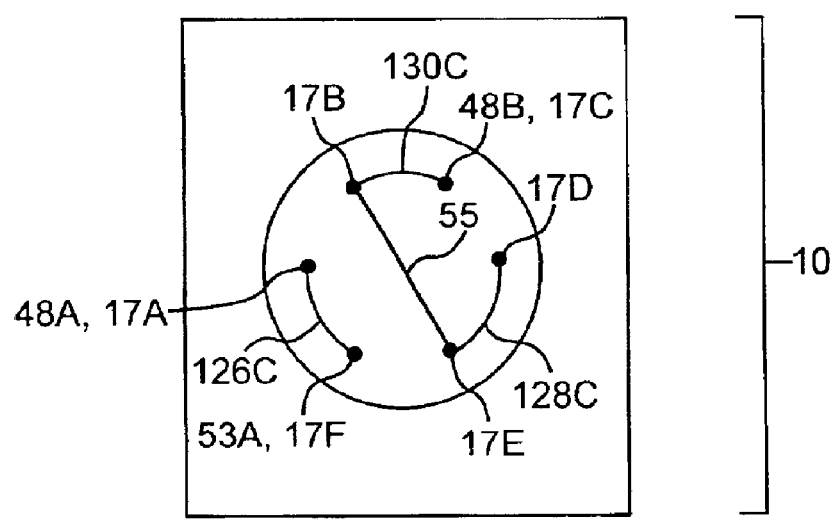

Depending on the relative orientation of the switching plate and the substrate, at least two possible flow paths configurations can be created. As shown in FIG. 4B, the first flow path configuration allows a first mobile phase from a first mobile-phase source to travel, in order, through conduit 48A, conduit 17A, conduit 126C, conduit 17B, conduit 55, conduit 17E, conduit 128C, conduit 17F and conduit 53A. The first flow path configuration also allows a second mobile phase from a second mobile-phase source (not shown) to travel, in order, through conduit 48B, conduit 17C, conduit 130C, and conduit 17D. Typically, the first and second mobile-phase sources contain differing concentrations of a mobile phase component. By rotating the switching plate 120 60° about its center, a second flow path configuration results, as shown in FIG. 4C. The second flow path configuration allows the first mobile phase to travel, in order, through conduit 48A, conduit 17A, conduit 126C, conduit 17F, and conduit 53A. In addition, the second flow path configuration allows the second mobile phase to travel, in order, through conduit 48B, conduit 17C, conduit 130C, conduit 17B, conduit 55, conduit 17E, conduit 128C and conduit 17D.

In use, the switching plate 120 of the switching structure is arranged to result in a first flow path configuration as discussed above. A pressurizing means deliver a second mobile phase from a second mobile-phase source through mobile phase inlet conduit 48B, conduit 17C, conduit 130C, and conduit 17D. In addition, a first mobile phase is conveyed from the first mobile-phase source through conduit 48A. As a result, the first mobile phase forms a contiguous body of fluid that flows, through conduit 48A, conduit 17A, conduit 126C, conduit 17B, conduit 55, conduit 17E, conduit 128C, conduit 17F and conduit 53A. The mobile phase emerging from conduit 53A may be collected and recycled. Thus, conduit 55 is filled with a plug of the first mobile phase.

By forming a second flow path configuration as discussed above, the conduit 55 is now positioned in the flow path of the mobile phase entering the switching structure through conduit 48B. That is, the second mobile phase is now pumped through a flow path that travels, in order, through conduit 48B, conduit 17C, conduit 130C, conduit 17B, conduit 55, conduit 17E, conduit 128C and conduit 17D. Thus, the first mobile phase within conduit 55 is also forced through conduit 17D. It should be evident, then, that by rotating the substrate of the switching assembly, a first mobile-phase plug having a volume defined by conduit 55 is controllably introduced from a first mobile-phase source through conduit 17D followed by a second mobile phase. By providing fluid communication between conduit 17D and an inlet of a mobile-phase holding conduit (not shown), the mobile-phase holding conduit may be filled with a mobile phase that contains a first mobile-phase plug downstream from a second mobile-phase plug, thereby forming an overall mobile phase, contained in the mobile-phase holding conduit, that exhibits differing concentrations of a mobile phase component.

FIG. 5, illustrate a switching structure that employs rotational motion to controllably introduce plug of a first mobile phase, followed by, in order, a plug of a second mobile phase and the first mobile phase through a conduit. Like the switching structure illustrated in FIG. 4, the switching structure illustrated in FIG. 5 also employs rotational motion to controllably introduce a plug of a mobile phase. The switching structure 10 includes a substrate 12 and a switching plate 120 each having contact surface in slidable and fluid-tight relationship with each other. Eight conduits indicated at 17A, 17B, 17C, 17D, 17E, 17F, 17G and 17H, extend through the substrate and represent the vertices of an equilateral octagon.

The contact surface of the switching plate has located thereon four curved fluid-transporting channels. The four fluid-transporting channels lie along a circle having a diameter equal to the distance between two substrate conduits located farthest from each other. As a result, the fluid-transporting channels, in combination with substrate contact surface, form four conduits, 126C, 128C, 130C and 132C, as shown in FIG. 5.

Figure 5A:
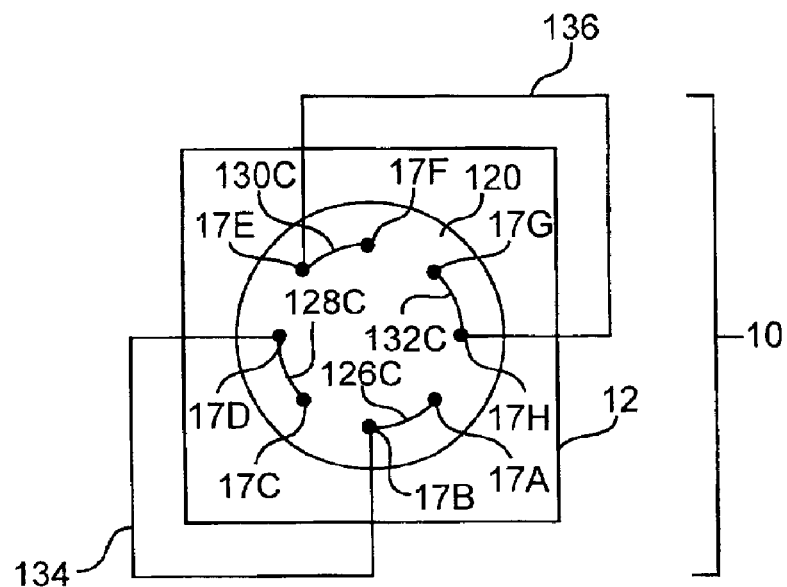
FIGS. 5A and 5B, collectively referred to as FIG. 5, illustrate a switching structure that employs rotational motion to controllably introduce, through a conduit, a plug of a first mobile phase, followed by a plug of a second mobile phase and the first mobile phase.
Figure 5B:
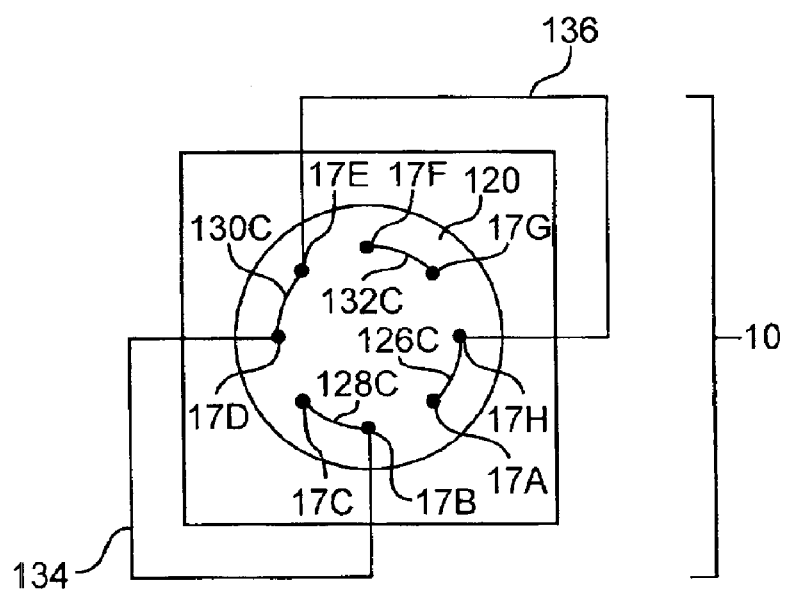

Furthermore, two microconduits, indicated at 134 and 136, are provided as plug-holding chambers. Microconduit 134 provides fluid communication between substrate conduits 17B and 17D, and microconduit 136 provides fluid communication between substrate conduits 17E and 17H. Such microconduits may comprise, for example, commercially available capillary tubing. Depending on the relative orientation of the switching plate and the substrate, at least two possible flow paths configurations can be created. As shown in FIG. 5A, the first flow path configuration allows a first mobile phase from a first mobile-phase source (not shown) to travel, in order, through conduit 17A, conduit 126C, conduit 17B, conduit 134, conduit 171D, conduit 128C and conduit 17C. The first flow path configuration also allows a second mobile phase from a second mobile-phase source (not shown) to travel, in order, through conduit 17G, conduit 132C, conduit 17H, conduit 136, conduit 17E, conduit 130C, and conduit 17F. This configuration allows plug-holding chamber 134 to be filled by the first mobile phase and plug holding chamber 136 to be filled by the second mobile phase. By rotating the switching plate 120 450° about its center, a second flow path configuration results, as shown in FIG. 5B. The second flow path configuration forms a first flow path extending, in order, through conduit 17A, conduit 126C, conduit 17H, conduit 136, and conduit 17E, conduit 130C, conduit 171D, conduit 134, conduit 17B, conduit 128C and conduit 17C. The second flow path configuration also forms a second flow path extending, in order, through conduit 17G, conduit 132C, and conduit 17F. Thus, by rotating the substrate of the switching assembly, a first mobile-phase plug defined by conduit 134 is introduced through conduit 17C followed by a second mobile-phase plug defined by conduit 136, which is followed by additional first mobile phase. By providing fluid communication between conduit 17C and an inlet of a mobile-phase holding conduit (not shown), the mobile-phase holding conduit may be filled with a mobile phase that contains a first mobile-phase plug downstream from a second mobile-phase plug, which is downstream from an additional first mobile-phase plug, thereby forming an overall mobile phase, contained in the mobile-phase holding conduit, that exhibits differing concentrations of a mobile phase component.

Thus, the invention provides, in yet another embodiment, a method for producing a flow of mobile phase. A mobile-phase source is provided comprising a mobile-phase-holding microconduit having a length defined by an upstream terminus and a downstream terminus, and an outlet port located at the downstream terminus, and a mobile phase, contained in the mobile-phase holding microconduit that exhibits differing concentrations of selected mobile-phase component along the length of the microconduit a substrate. The mobile-phase holding microconduit is pressurized to force the mobile phase within the mobile-phase holding microconduit to flow toward the downstream terminus along the length of the microconduit and out of the outlet port. Optionally, at least one inlet port is provided fluid communication with the mobile-phase holding microconduit, wherein the outlet port is located downstream from the at least one inlet port of the mobile-phase holding microconduit. In such a case, a plurality of mobile-phase sources may be provided as well, each containing a mobile phase, wherein each mobile phase contains a different concentration of a selected mobile-phase component. Plugs of mobile phase from the mobile-phase sources are introduced through the at least one inlet port into the mobile-phase holding microconduit such that the plugs are arranged in a predetermined order along the length of the mobile-phase holding conduit.

In any of the above embodiments, suitable materials for forming the substrates and cover plates are selected with regard to physical and chemical characteristics that are desirable for proper functioning of the microfluidic device. In all cases, the substrate must be fabricated from a material that enables formation of high definition (or high "resolution") features, i.e., microchannels, chambers, and the like, that are of micrometer or submicrometer dimensions. That is, the material must be capable of microfabrication using, e.g., dry etching, wet etching, laser etching, laser ablation, molding, embossing, or the like, so as to have desired miniature surface features; preferably, the substrate is capable of being microfabricated in such a manner as to form features in, on, and/or through the surface of the substrate. Microstructures can also be formed on the surface of a substrate by adding material thereto. For example, polymer channels can be formed on the surface of a glass substrate using photo-imageable polyimide. In addition, a plurality of pieces or layers may be assembled to result in the formation of a substrate having a feature in, on, and/or through the surface of the substrate. Thus, for example, a substrate having a channel located on a surface thereof may be formed from two layers, a first solid layer affixed to a second layer having a through-hole that in combination with the first solid layer form the channel. Also, all device materials that are used should be chemically inert and physically stable (e.g., in terms of pH, electric fields, etc.) with respect to any substance with which they come into contact when used to introduce a fluid sample. Suitable materials for forming the present devices include, but are not limited to, polymeric materials, ceramics (including aluminum oxide and the like), glass, metals, composites, and laminates thereof.

Polymeric materials are particularly preferred herein, and will typically be organic polymers that are either homopolymers or copolymers, whether naturally occurring or synthetic, and crosslinked or uncrosslinked. Specific polymers of interest include, but are not limited to, polyimides, polycarbonates, polyesters, polyamides, polyethers, polyurethanes, polyfluorocarbons, polystyrenes, poly (acrylonitrile-butadienestyrene)(ABS), acrylate and acrylic acid polymers such as polymethyl methacrylate, other substituted and unsubstituted polyolefins, and copolymers thereof. Generally, at least one of the substrate and cover plate comprises a biofouling-resistant polymer when the microfluidic device is employed to transport biological fluids. Polyimide is of particular interest and has proven to be a highly desirable substrate material in a number of contexts. Polyimides are commercially available, e.g., under the tradename Kapton®, (DuPont, Wilmington, Del.) and Upilex® (Ube Industries, Ltd., Japan). Polyetheretherketones (PEEK) also exhibit desirable biofouling-resistant properties.

The devices of the invention may also be fabricated from a "composite," i.e., a composition comprised of unlike materials. The composite may be a block composite, e.g., an A-B-A block composite, an A-B-C block composite, or the like. Alternatively, the composite may be a heterogeneous combination of materials, i.e., in which the materials are distinct separate phases; or it may be a homogeneous combination of unlike materials. As used herein, the term "composite" is used to include a "laminate" composite. A "laminate" refers to a composite material formed from several different bonded layers of identical or different materials. Other preferred composite substrates include polymer laminates, polymer-metal laminates (e.g., polymer coated with copper), ceramic-in-metal composites, or polymer-in-metal composites. One preferred composite material is a polyimide laminate formed from a first layer of polyimide, such as Kapton®, that has been co-extruded with a second, thin layer of a thermal adhesive form of polyimide known as KJ®, also available from DuPont (Wilmington, Del.).

The present microfluidic devices can be fabricated using any convenient method, including, but not limited to, micromolding and casting techniques, embossing methods, surface micromachining, and bulk-micromachining. The latter technique involves formation of microstructures by etching directly into a bulk material, typically using wet chemical etching or reactive ion etching ("RIE"). Surface micromachining involves fabrication from films deposited on the surface of a substrate. An exemplary surface micromachining process is known as "LIGA." See, for example, Becker et al. (1986), "Fabrication of Microstructures with High Aspect Ratios and Great Structural Heights by Synchrotron Radiation Lithography Galvanoforming and Plastic Moulding (LIGA Process)," *Microelectronic Engineering* 4(1) :35–36; Ehrfeld et al. (1988), "1988 LIGA Process: Sensor Construction Techniques via X-Ray Lithography," *Tech. Digest from IEEE Solid-State Sensor and Actuator Workshop,* Hilton Head, S.C.; Guckel et al. (1991) *J. Micromech. Microeng.* 1:135–138. LIGA involves deposition of a relatively thick layer of an X-ray resist on a substrate followed by exposure to high-energy X-ray radiation through an X-ray mask, and removal of the irradiated resist portions using a chemical developer. The LIGA mold so provided can be used to prepare structures having horizontal dimensions--i.e., diameters—on the order of micrometers.

Another technique for preparing the present microfluidic devices is laser ablation. In laser ablation, short pulses of intense ultraviolet light are absorbed in a thin surface layer of material. Preferred pulse energies are greater than about 100 millijoules per square centimeter, and preferred pulse durations are shorter than about 1 microsecond. Under these conditions, the intense ultraviolet light photo-dissociates the chemical bonds in the substrate surface. The absorbed ultraviolet energy is concentrated in such a small volume of material that it rapidly heats the dissociated fragments and ejects them away from the substrate surface. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micrometer or less. Laser ablation will typically involve use of a high-energy photon laser, such as an excimer laser of the $F_2$, ArF, KrCl, KrF, or XeCl type. However, other ultraviolet light sources with substantially the same optical wavelengths and energy densities may be used as well. Laser ablation techniques are described, for example, by Znotins et al. (1987) *Laser Focus Electro Optics,* at pp. 54–70, and in U.S. Pat. Nos. 5,291,226 and 5,305,015 to Schantz et al.

The fabrication technique that is used must provide for features of sufficiently high definition, i.e., microscale components, channels, chambers, etc., such that precise "microalignment" of these features is possible, i.e., the features must be capable of precise and accurate alignment, including, for example, the alignment of complementary microchannels with each other, the alignment of projections and mating depressions, the alignment of grooves and mating ridges, and the like.

For any of the inventive devices, the fluid-transporting features may be formed, independently or otherwise, through laser ablation or other techniques discussed below or known in the art. It will be readily appreciated that, although the microchannels have been represented in a generally extended form, microchannels for this and other embodiments can have a variety of configurations, such as a straight, serpentine, spiral, or any tortuous path. Further, the microchannels can be formed in a wide variety of crosssectional channel geometries, including semi-circular, rectangular, rhomboidal, and the like; and the channels can be formed in a wide range of aspect ratios.

In some instances, the substrate and the cover plate may be formed in a single, solid flexible piece. Microfluidic devices having a single-piece substrate and cover plate configuration have been described, e.g., in U.S. Pat. Nos. 5,658,413 and 5,882,571, each to Kaltenbach et al. However, the cover plate and substrate of the inventive device are typically formed as discrete components. In such a case, microalignment means described herein or known to one of ordinary skill in the art may be employed to align the cover plate with the substrate. To ensure that the conduit or conduits formed between the substrate and the cover plate are fluid-tight, pressure-sealing techniques may be employed, e.g., by using external means (such as clips, tension springs, or an associated clamp), internal means (such as male and female couplings), or chemical means (e.g., adhesive or welding) to hold the pieces together. As with all embodiments described herein, the pressure-sealing techniques may allow the contact surfaces to remain in fluid-tight contact under an internal microfluidic device fluid pressure of up to about 100 megapascals, typically about 0.5 megapascals to about 40 megapascals.

The separation conduit for the inventive device is constructed for separation as generally described in U.S. Ser. No. 09/908,231. Aspects of known separation technology may be incorporated in the practice of the present invention. For example, the microfluidic device may further comprise separation media within a separation conduit, or a polymeric material formed in situ within the separation conduit. When ordinary liquid chromatography packing material is slurry-packed within the separation conduit, a frit structure, micromachined or otherwise, may be included near or at the sample outlet port. The frit structure serves to ensure that the packing material is not displaced from within the sample conduit when a fluid sample and/or a mobile phase are conveyed through the conduit. In addition, it is preferred that the cross-sectional area of the separation conduit be reduced downstream from the frit structure, particularly if the sample outlet port is a part of an electrospray tip as described, for example, in U.S. Ser. No. 09/711,804 ("A Microfluidic device Having an Integrated Protruding Electrospray Emitter and a Method for Producing the Microfluidic device"), inventors Brennen, Yin, and Killeen, filed on Nov. 13, 2000. Alternatively, the separation conduit may exhibit a high surface area-to-volume ratio.

Thus, the conduit may exhibit any micromachined structure appropriate for liquid chromatography. In addition, or in the alternative, the conduit may contain any of a number of known liquid chromatographic packing materials. Such packing materials typically exhibit a surface area of about 100 $m^2/g$ to about 500 $m^2/g$. The conduit may be adapted to separate fluid sample components according to molecular weight, polarity, hydrophobicity, or other properties through techniques known to one of ordinary skill in the art (e.g., through proper selection of packing materials).

Similarly, an analyzer may be interfaced with any portion of the flow path of the inventive microfluidic device, including the inlet port. The analyzer may be, for example, a mass spectrometer, in which case the outlet port could be located within or adapted to deliver fluid sample to an ionization chamber. See U.S. Ser. No. 09/711,804 ("A Microfluidic device Having an Integrated Protruding Electrospray Emitter and a Method for Producing the Microfluidic device"), inventors Brennen, Yin, and Killeen, filed on Nov. 13, 2000. In addition, mass spectrometry technologies are well known in the art and may involve, for example, laser desorption and ionization technologies, for which uses in conjunction with microfluidic devices are described in U.S. Pat. Nos. 5,705,813 and 5,716,825. In the alternative or in addition, the analyzer may be a source of electromagnetic radiation configured to generate electromagnetic radiation of a predetermined wavelength. Depending on the intrinsic properties of the fluid sample and/or any molecular labels used, the radiation may be ultraviolet, visible, or infrared radiation.

From the above description of the various embodiments of the invention, it is evident that a sample-introducing means appropriate to the desired separation process and the dimensions of the microfluidic device may be used to introduce a predetermined volume of fluid sample. Typically, the predetermined volume is less than about 5 $\mu L$. Preferably, the predetermined volume is about 0.005 $\mu L$ to about 1 $\mu L$. Optimally, the predetermined volume is about 0.01 $\mu L$ to about 0.1 $\mu L$. Examples of sample-introducing means are described in U.S. Ser. Nos. 09/908,231 and 09/908,292. Additional sample-introducing means include, but are not limited to, syringes, micropipettes, inkjet printheads, sippers, and other devices known in the art.

Variations of the invention, not explicitly disclosed herein, will be apparent to those of ordinary skill in the art.

Other features may be included to carry out known reactions and processes, for example, reactions and processes associated with sample preparation, synthesis, and analysis. Such features may be formed from conduits and channels that provide for fluid flow in a parallel or a nonparallel direction with respect to the contact surfaces. Moreover, cascades may be formed as channels on a single substrate surface, as features on a switching mechanism, or as an assembly of conduits formed as a distinct and separate from the separation column. In addition, one of ordinary skill may adapt the structures and the components of structures discussed above to operate in combination, optionally with other microfluidic flow control mechanisms. In addition to the use of diffusion to create a gradient, micromixers known the art may be incorporated to accelerate mixing.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

We claim:

1. A microfluidic device for separating the components of a fluid sample, the microfluidic device comprising:

a substrate having a microchannel formed in a surface thereof;

a cover plate arranged over the substrate surface, the cover plate in combination with the microchannel defining a separation conduit for separating the components of the fluid sample according to a specific component property, wherein the separation conduit has an inlet port and an outlet port; and an integrated gradient-generation means for generating a gradient of a selected mobile-phase component in a mobile phase by the use of pressure driven flow, including a mechanical switching structure adapted to allow the mobile phase from the gradient-generation means to be transported through the inlet port into the separation conduit and out of the outlet port.

2. The microfluidic device of claim 1, wherein the integrated gradient-generation means is formed at least in part within the substrate.

3. The microfluidic device of claim 1, wherein the integrated gradient-generation means is formed at least in part in the cover plate.

4. The microfluidic device of claim 1, wherein the integrated gradient-generation means comprises:

a mobile-phase holding conduit having a length defined by an upstream terminus and a downstream terminus;

a plurality of mobile-phase inlet ports arranged along the length of the mobile-phase holding conduit;

a mobile-phase outlet port located downstream from the mobile-phase inlet ports; and the mechanical switching structure introducing the mobile phase from the mobile-phase holding conduit through the mobile-phase outlet port and into the inlet port of the separation conduit.

5. The microfluidic device of claim 4, wherein the mobile-phase inlet ports are evenly spaced along the length of the mobile-phase holding conduit.

6. The microfluidic device of claim 4, wherein no mobile-phase inlet port is located at the upstream terminus of the mobile-phase holding conduit.

7. The microfluidic device of claim 4, wherein no mobile-phase inlet port is located at the downstream terminus of the mobile-phase holding conduit.

8. The microfluidic device of claim 4, wherein the gradient-generation means further comprises a distribution conduit in fluid communication with the mobile-phase holding means.

9. The microfluidic device of claim 8, wherein the distribution conduit is substantially parallel to the mobile-phase holding conduit.

10. The microfluidic device of claim 8, wherein the distribution conduit further comprises a plurality of outlet ports, each fluidly communicating via a mixing conduit with an inlet port of the mobile-phase conduit.

11. The microfluidic device of claim 10, wherein the distribution conduit further comprises an inlet port located between each of its outlet ports.

12. The microfluidic device of claim 8, wherein the distribution conduit comprises two inlet ports.

13. The microfluidic device of claim 12, further comprising two mobile-phase sources in fluid communication with the integrated gradient-generation means, wherein at least one of the mobile-phase sources contains the selected mobile-phase component.

14. The microfluidic device of claim 13, wherein one of the mobile-phase sources does not contain the selected mobile-phase component.

15. The microfluidic device of claim 13, wherein one of the mobile-phase sources contains the selected mobile-phase component in a substantially pure form.

16. The microfluidic device of claim 1, further comprising a means for controlling fluid communication between the gradient-generation means and the separation conduit.

17. The microfluidic device of claim 1, further comprising separation media within the separation conduit.

18. The microfluidic device of claim 1, further comprising a polymeric material formed in situ within the separation conduit.

19. The microfluidic device of claim 1, wherein the separation conduit exhibits a high surface area-to-volume ratio.

20. The microfluidic device of claim 1, wherein the component property is selected from the group consisting of molecular weight, polarity, hydrophobicity, and charge.

21. A microfluidic device for separating the components of a fluid sample, the microfluidic device comprising:
(a) a gradient-generation means for generating a gradient of a selected mobile-phase component in a mobile phase by the use of pressure driven flow comprising
(i) a substrate having a microchannel formed in a surface thereof, wherein the microchannel has an upstream terminus and a downstream terminus,
(ii) a cover plate arranged over the substrate surface, wherein the cover plate, in combination with the microchannel, forms a mobile-phase holding conduit having a length defined by the upstream terminus and the downstream terminus,
(iii) a plurality of inlet ports arranged along the length of the mobile-phase holding conduit, and
(iv) an outlet port located downstream from the inlet ports of the mobile-phase holding conduit;
(b) a separation conduit for separating the components of a fluid sample according to a specific component property; and
(c) a mechanical switching structure for introducing the mobile phase from the gradient-generation means into the separation conduit.

22. A microfluidic device for separating the components of a fluid sample, the microfluidic device comprising:
a substrate having a microchannel formed in a surface thereof;
a cover plate arranged over the substrate surface, such that the cover plate, in combination with the microchannel, defines a separation conduit for separating the components of the fluid sample according to a specific component property, wherein the separation conduit has an inlet port and an outlet port; and
an integrated mobile-phase source comprising a microconduit having a length defined by an upstream terminus and a downstream terminus, the microconduit containing a mobile phase that exhibits a gradient of a selected mobile-phase component along the length of the microconduit, wherein the gradient is generated by the use of a mechanical switching structure to provide pressure driven flow,
wherein the integrated mobile-phase source is arranged to allow the mobile phase to be transported through the inlet port into the separation conduit and out of the outlet port.

23. A microfluidic device for producing a flow of mobile phase:
(a) mobile-phase source comprising
(i) a mobile-phase holding microconduit having a length defined by an upstream terminus and a downstream terminus, and an outlet port located at the downstream terminus, and
(ii) a mobile phase, contained in the mobile-phase holding microconduit, that exhibits differing concentrations of selected mobile-phase component along the length of the mobile-phase holding microconduit, wherein the differing concentrations are generated by the use of pressure driven flow; and
(b) a mechanical switching structure for pressurizing the microconduit to force the mobile phase within the microconduit to flow toward the downstream terminus along the length of the microconduit and out the outlet port.

24. The microfluidic device of claim 23, further comprising a separation conduit in fluid communication with the outlet port of the microconduit.

25. The microfluidic device of claim 23, wherein the microconduit is further defined by a substrate having a microchannel formed in a surface thereof in combination with a cover plate arranged over the substrate surface.

26. A microfluidic device for producing a flow of mobile phase, the microfluidic device comprising:
(a) a means for producing different concentrations of a selected mobile-phase component in different locations within a mobile phase by the use of pressure driven flow, comprising
(i) a mobile-phase-holding microconduit having a length defined by an upstream terminus and a downstream terminus,
(ii) an outlet port located at the downstream terminus of the mobile-phase holding microconduit, and
(iii) at least one inlet port in fluid communication with the mobile-phase holding microconduit upstream from the outlet port;
(b) a plurality of mobile-phase sources each containing a mobile phase, wherein each mobile phase contains a different concentration of a selected mobile-phase component;

(c) a means for introducing plugs of mobile phase from the mobile-phase sources through the at least one inlet port into the mobile-phase holding conduit such that the plugs are arranged in a predetermined order along the length of the mobile-phase holding conduit; and (d) a mechanical switching structure for pressurizing the microconduit to force the mobile phase within the microconduit to flow toward the downstream terminus along the length of the microconduit and out the single outlet port.

27. The microfluidic device of claim 26, further comprising a separation conduit in fluid communication with the outlet port of the microconduit.

28. The microfluidic device of claim 26, wherein the mobile-phase holding microconduit is further defined by a substrate having a microchannel formed in a surface thereof in combination with a cover plate arranged over the substrate surface.

* * * * *